(12) United States Patent
Baillargeon et al.

(10) Patent No.: US 10,568,612 B2
(45) Date of Patent: Feb. 25, 2020

(54) DEVICE FOR CREATING A LOCAL VACUUM AT A DISTAL END OF A SAMPLING DEVICE

(71) Applicant: Spiration, INC., Redmond, WA (US)

(72) Inventors: Jean-Martin Baillargeon, Seattle, WA (US); Christopher J. Thralls, Kirkland, WA (US); Hugo Xavier Gonzalez, Woodinville, WA (US); Peter D. Hoffman, Seattle, WA (US); Clinton L. Finger, Bellevue, WA (US); Brandon Shuman, Kirkland, WA (US)

(73) Assignee: Spiration, INC., Redmond, WA (US)

( * ) Notice: Subject to any disclaimer, the term of this patent is extended or adjusted under 35 U.S.C. 154(b) by 212 days.

(21) Appl. No.: 15/558,256

(22) PCT Filed: Mar. 7, 2016

(86) PCT No.: PCT/US2016/021156
§ 371 (c)(1),
(2) Date: Sep. 14, 2017

(87) PCT Pub. No.: WO2016/153770
PCT Pub. Date: Sep. 29, 2016

(65) Prior Publication Data
US 2018/0042588 A1 Feb. 15, 2018

Related U.S. Application Data

(60) Provisional application No. 62/138,729, filed on Mar. 26, 2015.

(51) Int. Cl.
*A61B 10/02* (2006.01)
(52) U.S. Cl.
CPC ...... *A61B 10/0283* (2013.01); *A61B 10/0266* (2013.01); *A61B 2010/0208* (2013.01)

(58) Field of Classification Search
CPC ............ A61B 10/0283; A61B 10/0233; A61B 10/0266; A61B 2010/0208; A61B 10/02
(Continued)

(56) References Cited

U.S. PATENT DOCUMENTS

| 3,882,849 A | 5/1975 | Jamshidi |
| 4,643,196 A | 2/1987 | Tanaka et al. |

(Continued)

FOREIGN PATENT DOCUMENTS

| EP | 0186256 A1 | 7/1986 |
| JP | 2007521924 A | 8/2007 |

(Continued)

OTHER PUBLICATIONS

International Search Report and Written Opinion for International Application No. PCT/US2016/021156, dated May 25, 2016.
(Continued)

*Primary Examiner* — Navin Natnithithadha
(74) *Attorney, Agent, or Firm* — Robert R. Richardson, P.S.

(57) ABSTRACT

A device for tissue sampling that comprises a needle, a stylet and a sealing member. The needle comprises a distal tip, a proximal end, and one or more interior portions. The needle extends along a longitudinal axis extending between the distal tip and the proximal end. The stylet is moveably supported within the one or more interior portions of the needle. The sealing member Is moveably supported within the one or more interior portions of the needle and substantially conforms to the one or more interior portions, The distal tip is configured to obtain a tissue sample. The stylet and the sealing member are movable, along the longitudinal axis away from the distal tip so that a local vacuum is created at the distal tip so that obtained tissue samples can be aspirated into the needle.

20 Claims, 8 Drawing Sheets

(58) Field of Classification Search
USPC .................................. 600/565, 566, 567, 571
See application file for complete search history.

(56) References Cited

U.S. PATENT DOCUMENTS

| | | | |
|---|---|---|---|
| 5,159,933 A | 11/1992 | Hut | |
| 5,282,476 A * | 2/1994 | Terwilliger | A61B 10/0266 600/566 |
| 6,155,989 A | 12/2000 | Collins | |
| 7,390,306 B2 * | 6/2008 | Mark | A61B 10/0275 600/565 |
| 8,231,544 B2 * | 7/2012 | Mark | A61B 10/0275 600/565 |
| 8,357,103 B2 * | 1/2013 | Mark | A61B 10/0275 600/566 |
| 8,679,032 B2 * | 3/2014 | Mark | A61B 10/0275 600/566 |
| 2005/0080355 A1 | 4/2005 | Mark | |
| 2005/0182394 A1 | 8/2005 | Spero et al. | |
| 2007/0106176 A1 | 5/2007 | Mark et al. | |
| 2008/0300507 A1 | 12/2008 | Figueredo et al. | |
| 2012/0071868 A1 | 3/2012 | Fischer et al. | |
| 2013/0197394 A1 * | 8/2013 | Mark | A61B 10/0275 600/566 |

FOREIGN PATENT DOCUMENTS

| | | |
|---|---|---|
| JP | 2008/528207 A | 7/2008 |
| JP | 2008528207 A | 7/2008 |
| JP | 2012-523936 A | 10/2012 |
| WO | 89/10092 A1 | 11/1989 |
| WO | WO-2017129735 A1 * | 8/2017 ......... A61B 10/0045 |

OTHER PUBLICATIONS

Japanese Office Action for Japanese Application No. 2017-550121; dated Jan. 8, 2019.
Japanese Office Action for Japanese Application No. 2017-550121; dated Aug. 28, 2018.

* cited by examiner

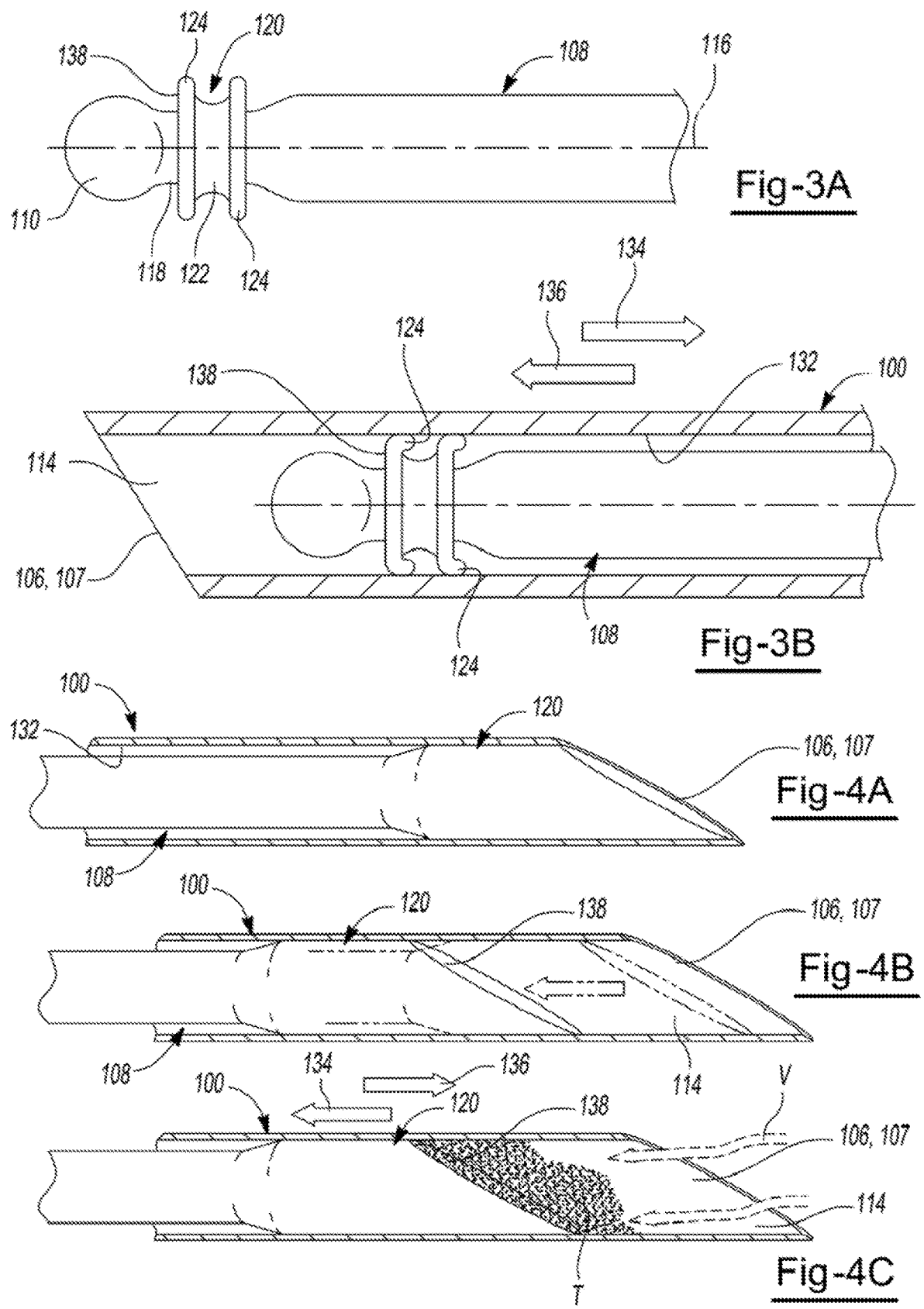

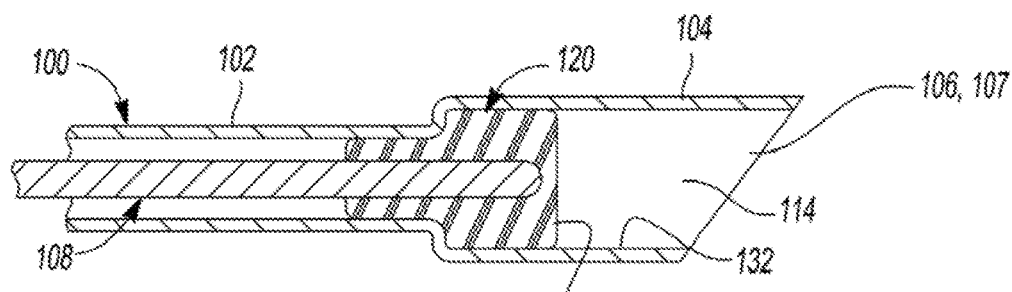
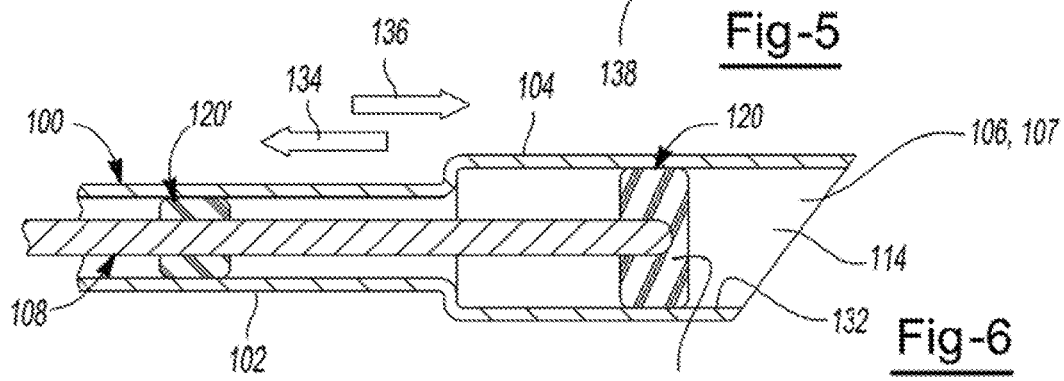
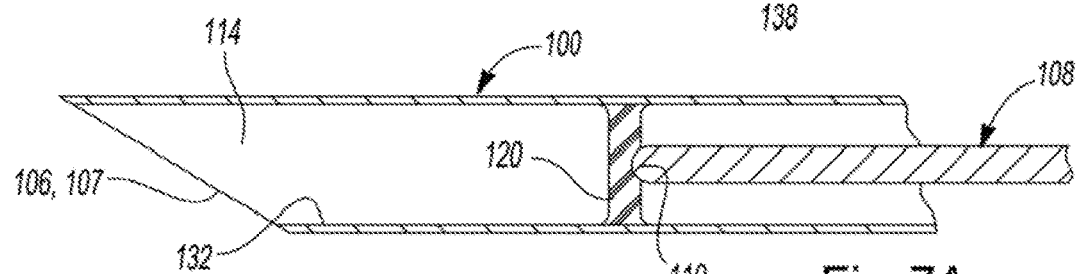
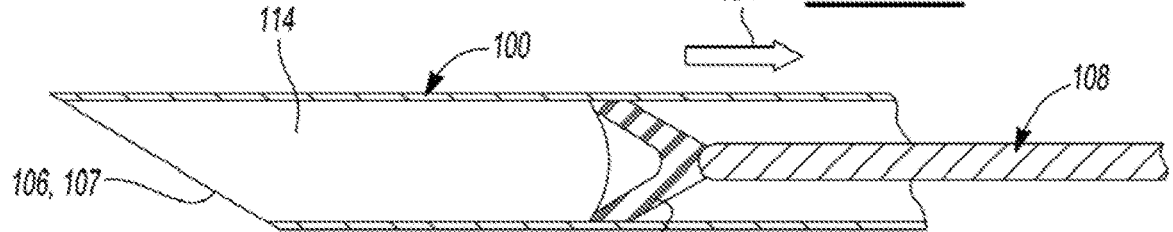
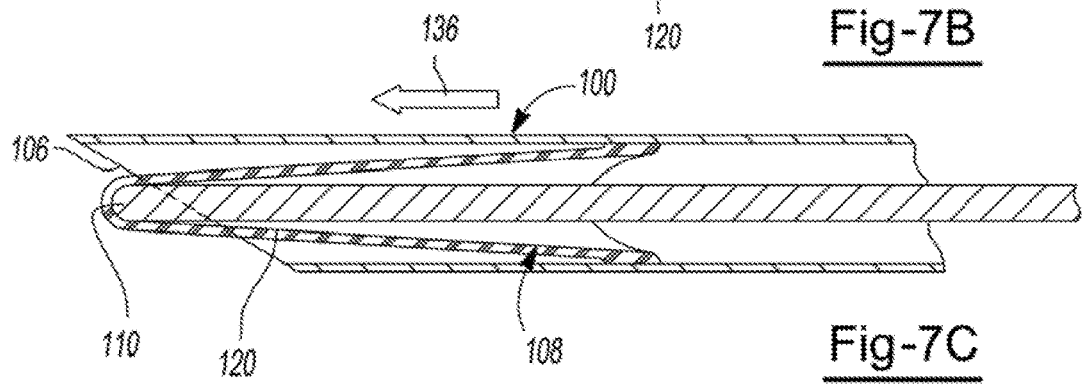

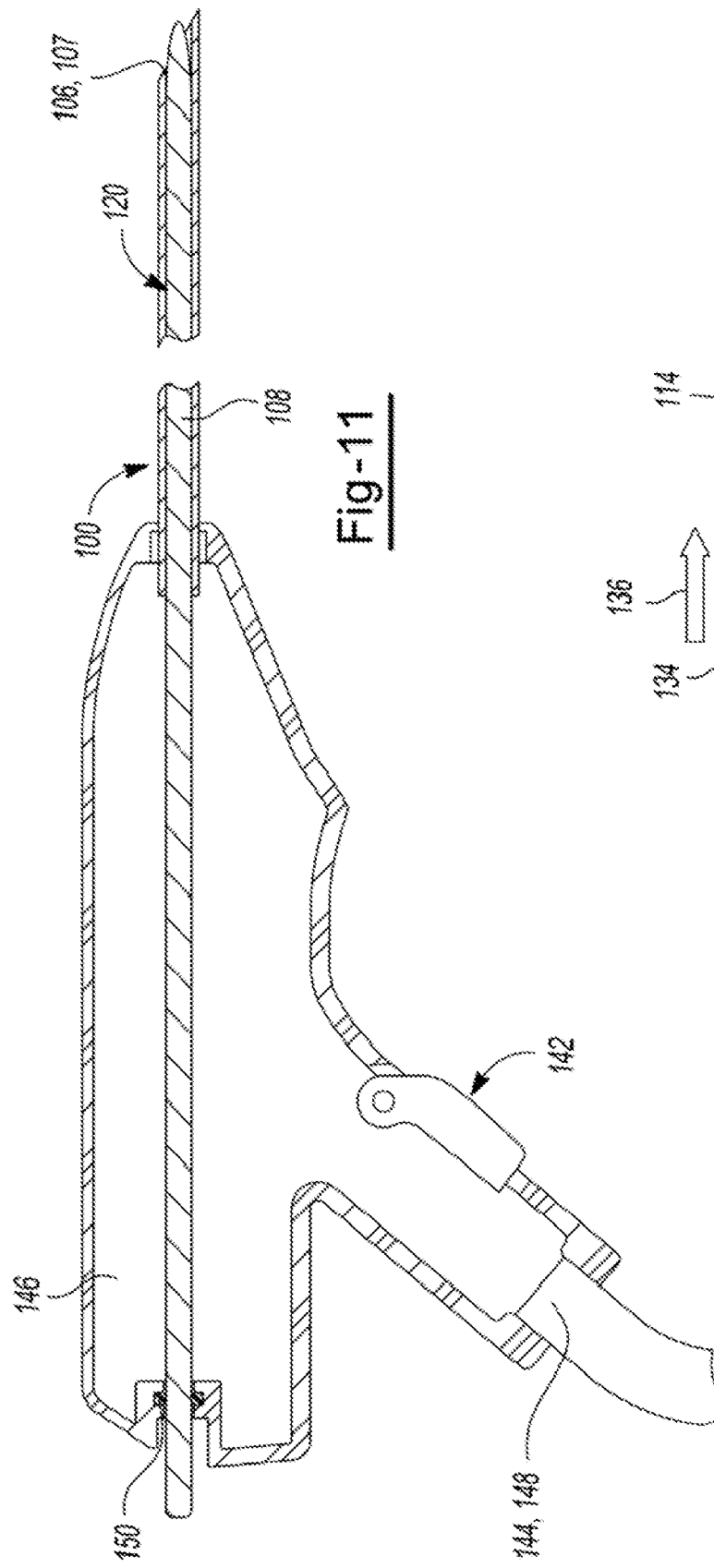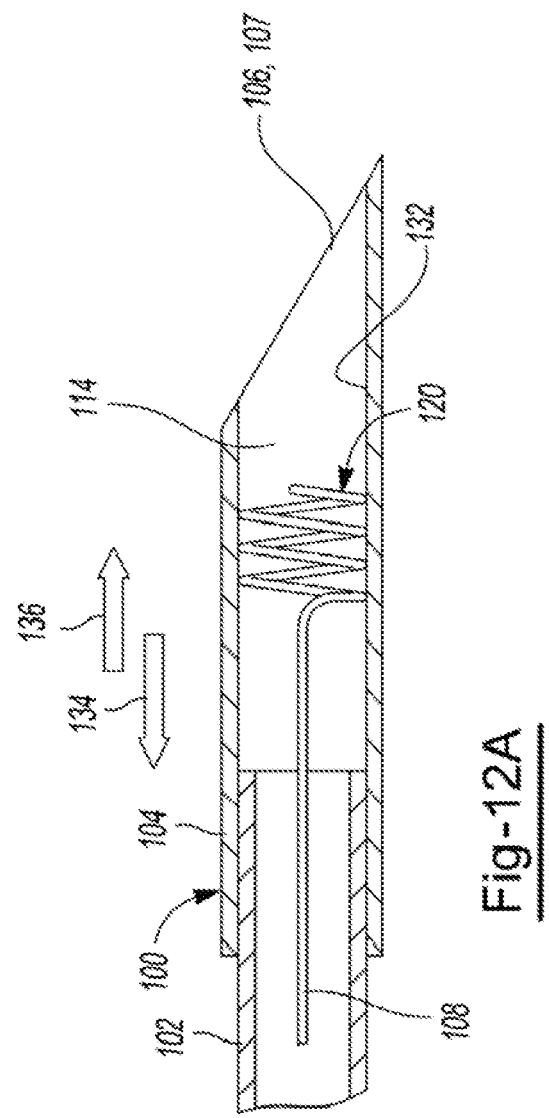

DEVICE FOR CREATING A LOCAL VACUUM AT A DISTAL END OF A SAMPLING DEVICE

FIELD

The present teachings relate to medical devices, and more particularly, to improved methods and devices for obtaining tissue samples from a site or region of interest.

BACKGROUND

To test a region of interest in a patient, it may be necessary to biopsy a tissue sample. When the region of interest is a lung, transbronchial needle aspiration ("TBNA") may be used to obtain a tissue sample from a lymph node. In TBNA, generally, a distal end of n bronchoscope is inserted through the patient's mouth and into the lung. A device, which may generally include a catheter, a general hollow needle disposed within the catheter, and a stylet disposed within the needle, can be inserted through a working channel of the bronchoscope and directed towards the lymph node. The stylet may be disposed within the needle such that the distal ends of the stylet and the needle are substantially aligned so that as the device is advanced towards the lymph node, the distal end of the stylet can block or prevent debris (i.e., tissue, blood, and the like) from entering the needle.

Once the device is near the lymph node, the stylet can be withdrawn from the needle so that a space for collecting tissue samples is created in the needle (i.e., a sample storage area). Once the stylet is withdrawn, an ancillary suction or vacuum device can be connected to a proximal end of the bronchoscope and/or the needle. The needle can then be advanced towards the lymph node so that a needle tip can penetrate, cut, core, and/or shear a tissue sample from the lymph node. The tissue sample can be aspirated into the sample storage area via the ancillary suction or vacuum device. Once a sufficient tissue sample is collected, the device can be removed from the bronchoscope. Once removed, negative suction can be applied to the device so that the sample tissue can be expelled from the needle and prepared for biopsy.

While the aforementioned devices and methods have proven satisfactory in the field, some difficulties exist. For example, in order to supply suction or vacuum to the sampling region, the stylet must be entirely withdrawn from the needle before the ancillary suction device can be attached. Because the stylet can be long, withdrawing the stylet from the needle can be cumbersome and may undesirably add time to the procedure. Moreover, subsequently attaching the suction device to the needle can also be cumbersome and add additional time to the procedure. Further, as the needle is advanced towards the lymph node, the needle may errantly penetrate blood vessels causing unnecessary bleeding. The application of suction may then aspirate blood into the sample storage area and deep into the needle, which may undesirably contaminate any collected tissue samples and/or make the collected tissue samples more difficult to process. In such a case, the device is typically removed from the bronchoscope and the patient, a fresh device is loaded into the bronchoscope and the patient, and another attempt is made to penetrate the lymph node. The application of suction may also aspirate tissue samples beyond the sample storage area and deep into the needle, which may make expelling the tissue sample difficult. This is especially true when the tissue samples are small and/or when the ancillary vacuum or suction device is difficult to control.

Accordingly, what is needed is a device that can create a local and controlled vacuum at a distal end of the device. What is needed is to provide a localized vacuum at a distal end of the device without attaching ancillary generators, equipment, and/or other external suction or vacuum devices. If would be desirable to provide a device that does not require entirely withdrawing the stylet from the needle in order to collect tissue samples. It would be desirable to provide a device that does not require entirely withdrawing the stylet from the needle in order to aspirate tissue samples into the sample storage area. It would be attractive to provide an improved tissue-sampling device suitable for use in transbronchial needle aspiration procedures. It would be attractive to prevent aspirating tissue samples past a sample storage area in a sampling needle. It would be desirable to provide a device that can be mass-produced relatively inexpensively, that has a minimal number of parts, and that is easy to operate. It would be desirable to provide a method for obtaining a tissue sample from a site or region of interest for biopsy.

While U.S. Patent Application Publication Numbers 2011/0144661 and 2014/0081318 appear to provide tissue-sampling devices, the teachings of which are entirely incorporated by reference herein for all purposes, these devices appear to have or include one or more of the aforementioned difficulties. Moreover, unfortunately, these devices do not appear to solve or provide any of the desired improvements previously described.

SUMMARY

The present teachings meet one or more of these needs by providing a device that can create a local and controlled vacuum at a distal end of the device. The present teachings provide a localized vacuum at a distal end of the device without the need for attaching ancillary generators, equipment, and/or one or more external suction or vacuum devices. The present teachings provide a device that does not require entirely withdrawing the stylet from the needle in order to collect tissue samples. The present teachings provide a device that does not require entirely withdrawing the stylet from the needle in order to aspirate tissue samples into the sample storage area. The present teachings provide an improved tissue-sampling device suitable for use in transbronchial needle aspiration procedures. The present teachings provide a device that can prevent aspirating tissue samples past a sample storage area in a sampling needle. The present teachings provide a device that can be mass-produced relatively inexpensively, that has a minimal number of parts, and that is easy to operate. Further yet, the present teachings provide a method for obtaining a tissue sample from a site or region of interest for biopsy.

The present teachings also provide a device for tissue sampling comprising a needle, a stylet and a sealing member. The needle comprises a distal tip, a proximal end, and one or more interior portions. The needle extends along a longitudinal axis extending between the distal tip and the proximal end. The stylet is moveably supported within the one or more interior portions of the needle. The sealing member is moveably supported within the one or more interior portions of the needle and substantially conforms to the one or more interior portions. The distal tip is configured to obtain a tissue sample. The stylet and the sealing member are movable along the longitudinal axis away from the distal tip so that a local vacuum is created at the distal tip so that obtained tissue samples can be aspirated into the needle.

The present teachings further provide a method for tissue sampling. The method comprises providing a device for tissue sampling comprising a needle including a distal tip, a proximal end, and a shaft having a longitudinal axis extending between the distal tip and the proximal end. A stylet is moveably supported within an interior portion of the shaft, and a sealing member is moveably supported within the interior portion of the shaft and substantially conforming to the interior of the shaft. The distal tip is configured to obtain a tissue sample, and the stylet and the sealing member are movable along the longitudinal axis away from the distal tip so that a local vacuum is created at the distal tip that aspirates the tissue samples into the needle. The method further comprises inserting the needle into and orienting the distal tip near a feature of interest; obtaining the tissue sample from the feature of interest; moving the stylet and the sealing member along the longitudinal axis away from the distal tip to create the local vacuum; and aspirating the tissue sample into the needle.

BRIEF DESCRIPTION OF THE DRAWINGS

FIG. 3A illustrates a cross-sectional view of a stylet and a sealing member for use with a needle according to the teachings herein;

FIG. 3B illustrates a cross-sectional view of a needle, a stylet, and a sealing member according to the teachings herein;

FIG. 4A illustrates cross-sectional view of a needle, a stylet, and a sealing member according to the teachings herein;

FIG. 4B illustrates a cross-sectional view of a needle, a stylet, and a sealing member according to she teachings herein;

FIG. 4C illustrates a cross-sectional view of a needle, a stylet and a sealing member according to the teachings herein;

FIG. 5 illustrates a cross-sectional view of a needle, a stylet, and a sealing member according to the teachings herein;

FIG. 6 illustrates a cross-sectional view of a needle, a stylet, and a sealing member according to the teachings herein;

FIG. 7A illustrates a cross-sectional view of a needle, a stylet, and a sealing member according to the teachings herein;

FIG. 7B illustrates a cross-sectional view of a needle, a stylet and a sealing member according to the teachings herein;

FIG. 7C illustrates a cross-sectional view of a needle, a stylet and a sealing member according to the teachings herein;

FIG. 11 illustrates a cross-sectional view of a needle, a stylet, a y-port provided at a proximal end according to the teachings herein;

FIG. 12A illustrates a cross-sectional view of a needle, a stylet, and a sealing member according to the teachings herein;

Figure 1:
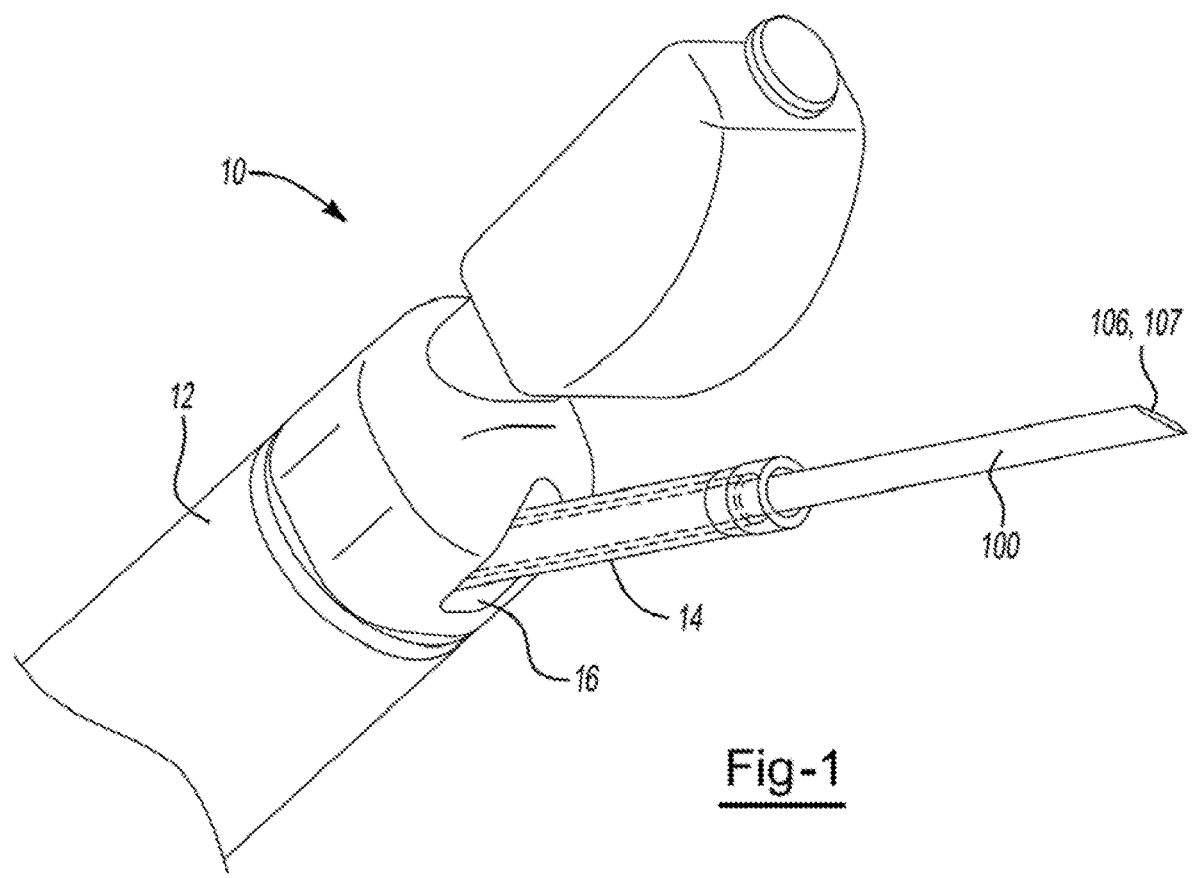
FIG. 1 illustrates a perspective view of a device including a bronchoscope having a needle according to the teachings herein.

It is understood that any of the teachings included in the individual figures can be separated or combined with the teachings included in other figures. In other words, the teachings included in a particular figure are not confined strictly to that figure; they can be introduced in addition to or instead of other features in any of the figures in this application.

DETAILED DESCRIPTION

This Application claims priority to U.S. Provisional Application No. 62/138,729, filed on Mar. 26, 2015, the entirely of which is hereby incorporated by reference herein for all purposes. The explanations find illustrations presented herein are intended to acquaint others skilled in the art with the teachings, its principles, and its practiced application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

While the teachings herein refer to and reference terms like "bronchoscope", "lymph node", "device", "needle", "sampling needle" and the like, it is understood that these terms are broad, and the teachings herein can be used without limitation. In other words, the teachings herein may be suitable for accessing other vessels, passages, lumens, body cavities, anatomy, tissue, organs, the like, or a combination thereof in humans and animals. The one or more devices may function to obtain tissue samples for biopsy. The one or more devices may function to obtain tissue samples, blood samples, or any other type of sample from internal organs such as the liver, lungs, pancreas, intestines, and kidneys. The one or more devices may function to inject or deliver medicine into the anatomy. The one or more devices may include one or more bronchoscopes.

The one or more bronchoscopes may be or may provide a device for withdrawing foreign bodies, tissue samples, or both from the anatomy. The one or more bronchoscopes may provide for insertion, manipulation, and operation of various surgical instruments in the anatomy of a patient. The one or more bronchoscopes may provide for delivery of one or more fluids, medicines, pastes, therapies, or a combination thereof into the anatomy. The one or more bronchoscopes may be used to visually inspect a site of interest, like the airways and lungs of a patient. The one or more bronchoscopes may be used to examine, treat, and/or diagnose lung growth, lung problems, lung cancer, lymph node(s), atelectasis, suspected interstitial lung disease, a lung rejection after a lung transplant, and/or to remove fluid or mucus plugs from the airways of a patient. The one or more bronchoscopes may be at least partially flexible, at least partially rigid, or both. The one or more bronchoscopes may include one or more ultrasound probes.

The one or more catheters may function to provide a channel, a lumen, an opening, and/or a passageway for one or more devices to be advanced and/or introduced into the anatomy. The one or more catheters may function to introduce into the anatomy one or more medical devices, needles, transbronchial needle aspiration devices, cytology brushes, biopsy forceps, guiding devices, ultrasonic probes, illumination devices, therapies (i.e., chemotherapy, proteinomics, microspheres, etc.), the like, or a combination thereof. The one or more catheters may be used to remove or expel from the anatomy one or more devices, fluids, tissue samples, abnormalities, foreign matter, or a combination thereof. The one or more catheters may each contain one or more lumen. The one or more catheters may include one or more sections that are generally rigid, one or more sections that are generally flexible, or a combination of both. The one or more catheters may include one or more sections that are generally rigid, generally flexible, or a combination of both. The one or more catheters may be at least partially flexible, bendable, articulable, or a combination thereof so that access to regions of interest can be easily obtained. The one or more catheters may bend or articulate 15 degrees or more, 45 degrees or more, 60 degrees or more, 90 degrees or more, 110 degrees or more, or even 130 degrees or more. The one or more catheters may be fabricated from a polymer, nylon, silicon, or any other suitable material. An outer surface of the one or more catheters may include a lubricant to facilitate insertion into, and removal from, the anatomy, the bronchoscope, the working channel of the bronchoscope, or a combination thereof. The one or more catheters may be elongated tubular members. The one or more catheters may extend along a longitudinal axis, a catheter axis, or both. The one or more catheters may include a uniform cross section, or the cross section may vary, taper, widen, narrow, or a combination thereof. The cross section of the one or more catheters may be circular, oval, irregular, and/or any other suitable shape or configuration. The cross section of the one or more catheters may be expandable, collapsible, formable, deformable, or a combination thereof. The one or more catheters may be configured to house, contain and/or protect any size or gauge needle. For example, the one or more catheters may house, contain, and/or protect, about a 25 gauge needle or more, about a 22 gauge needle, about a 21 gauge needle, about a 19 gauge needle or less, etc. An outer surface of the one or more catheters may include one or more echogenic features or scribes. The one or more catheters may include one or more echogenic features so that the position and orientation of the catheter, the device, the needle, the needle tip, or a combination thereof can be viewed. The one or more catheters may include or define a hole or opening at a distal end, a proximal end, at a region in between, or a combination thereof so that one or more devices or instruments can pass there through. The one or more catheters may include or define an inner surface, an inner diameter, an inner portion, or a combination thereof that is dimensioned to generally conform to the outer diameter of the one or more needles.

The one or more needles may function to be advanced into the anatomy to penetrate a site or region of interest. The one or more needles may function to puncture a region of interest so that a tissue sample can be obtained. The one or more needles may function to provide medicine, therapy, or both to the anatomy. The one or more needles may function to provide, develop, or have a local vacuum to a distal end or at a distal tip thereof. The one or more needles may be advanced towards and retracted from the region of interest via one or more catheters, devices, bronchoscopes, or a combination thereof. The one or more needles may be at least partially contained within the catheter. The one or more needles may be moved, advanced, retracted, or a combination thereof in the catheter. The one or more needles may have a length that extends along a longitudinal axis, a needle axis, or both. The one or more needles may have a constant cross section, a varying cross section, a tapered cross section, an irregular cross section, or a combination thereof. The cross section of the one or more needles may be generally circular, oval, irregular, or any other suitable shape. The one or more needles may be generally hollow. The one or more needles may include a generally concentric outer diameter and inner diameter. The one or more needles may have an outer diameter and an inner diameter, one or more of which may have a constant size along a length of the needle. The one or more needles may have an outer diameter and an inner diameter, one or more of which may vary, taper, slope, change, or a combination thereof. The one or more needles may be formed from a single material or may be formed from one or more materials. The one or more needles may be fabricated from any material suitable for use in medical procedures. The one or more needles may be made from a metal or metal alloy, such as stainless steel, nitinol, or the like. The one or more needles may comprise a polymer or other suitable covering. The one or more needles may be generally rigid, generally flexible, or both. The one or more needles may include one or more portions or sections that are generally rigid, one or more portions or sections that are generally flexible, or both. The one or more needles may be at least partially flexible, bendable, articulable, or a combination thereof so that access to regions of interest can be easily obtained. The one or more needles may bend or articulate about 15 degrees or more, about 45 degrees or more, about 60 degrees or more, about 0 degrees or more, about 110 degrees or more, or even about 130 degrees or more. The one or more needles may be constructed from one or more hypotubes. The one or more needles may be constructed from one or more hypotubes that are relatively smooth and able to freely slide, rotate, or otherwise move within a catheter, a bronchoscope, a device, the anatomy, or a combination thereof. The one or more needles may include one or more holes, ports, slots, apertures, openings, the like, or a combination thereof at the distal, end a proximal end, or a location therebetween. The one or more needles may include one or more holes, ports, slots, the like or a combination thereof for tissue sample collection; for introducing one or more devices into the needle; for introducing one or more devices into the anatomy; for introducing medicine or therapy to the anatomy; or a combination thereof.

The one or more needles may be any size or gauge. That is, the one or more needles may be about 25 gauge or more, about 22 gauge, about 21 gauge, or about 19 gauge or less, etc. The one or more needles may include a combination of two or more gauges. That is, for example, a proximal portion of the needle may be about 21 gauge and a distal, portion of the needle may be about 19 gauge, or vice versa. The one or more needles may comprise two or more needle portions that are joined together fixedly, permanently, temporarily, or a combination thereof. The two or more needle portions may be the same gauge, or may be different gauges. One or both of the needle portions may include an interior size or region that is generally the same size as the one or more stylets, sealing members, or both. That is, the one or more stylets, sealing members, or both may substantially occupy some, most, or all of the interior of the one or more needles, needle portions, or both. One or both of the needle portions, the needle, or both may be slightly larger than the one or more stylets, sealing members, or both so that the stylets, the sealing members, or both only occupy some of the interior space or region of the one or more needles, needle portions, or both. The one or more needles may include an elongated section, member, or shaft and a distal tip or needle tip. The elongated section, the needle tip, or both may include one or more, or even two or more echogenic markings or scribes. The one or more echogenic features may function to enhance the visibility of the catheter, the needle, the needle tip, or a combination thereof. The one or more echogenic features may function to create one or more echogenic reflections during ultrasonic imaging so that a portion or location of the catheter, the needle, and/or the needle tip within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof. The one or more needles may include a distal tip.

The distal end of the needle, the distal tip, the needle tip, or a combination thereof may be configured to function as a piercing tip or feature so that cells, tissue, foreign matter, or a combination thereof can be obtained. The needle tip may be angled, sharply angled, beveled, flat, or a combination thereof so that tissue samples can be cut, cored, scraped from a site or region of interest. The needle tip may include a notched portion, a recessed portion, and/or a lancet tip or feature. A local vacuum may be created or formed at a distal end of the needle, a distal portion, or a needle tip so that tissue samples, foreign matter, or both can be aspirated or moved into the needle, the sample storage area, or both. The one or more needle tips may be contained within the one or more catheters as the catheter is advanced through the anatomy towards the site or region of interest. The one or more needle tips may be advanced or extended past a distal end of the one or more catheters when the catheter is near the region of interest. The one or more needle tips may be generally rigid, flexible, or both. The distal end, the needle tip, or both may include one or more echogenic features. The one or more needles may include one or more sample storage areas.

The one or more sample storage areas may function to provide an area or location for cut, cored, separated, obtained, and/or removed tissue, foreign matter, or both from a site or region of interest to be stored. The one or more sample storage areas may function to provide an area for tissue samples, foreign matter, or both to be stored until the needle, catheter, bronchoscope, or a combination thereof are removed from the patient. The one or more sample storage areas may function to contain and protect the tissue sample. The tissue samples may be aspirated into the sample storage area via a local vacuum created at a distal end or needle tip of the needle, via an ancillary suction device in communication with the needle, or both. The one of more sample storage areas may be located between or next to a distal end or a needle tip of the needle and a distal end or distal surface of the stylet. The one or more sample storage areas may be located between or next to a distal end or needle tip of the needle and a distal end or distal surface of the sealing member. To create the one or more sample storage areas, the one or more stylets, sealing members or both may be at least partially moved and/or withdrawn from the one or more needles.

The one or more stylets may function to steer or guide the one or more needles, catheters, devices, or a combination thereof around the anatomy to the region of interest. The one or more stylets may be disposed within the needle such that the distal ends of the stylet and the needle are substantially aligned. The one or more stylets may function to block or prevent debris (i.e., tissue, blood, and the like) from entering the needle as needle is advanced towards a site or region of interest. The one or more stylets may be formed from a single material, or may be formed from one or more materials. The one or more stylets may be fabricated from any suitable material. The one or more stylets may be made from a metal or metal alloy, such as stainless steel, nitinol, or the like. The one or more stylets may be formed from a shape memory material (i.e., metal or polymer). The one or more stylets may comprise a polymer or other suitable covering over at least a portion of the length of the stylets. The one or more stylets may be at least partially rigid, at least partially flexible, or both. The one or more stylets may include one or more portions (i.e., a distal portion, a proximal portion, or a portion in between) that are at least partially rigid, at least partially flexible, or both. The one or more stylets may be at least partially flexible, bendable, articulable, or a combination thereof so that the stylet can be positioned along a central lumen, opening, and/or interior portion of the needles. The one or more stylets may bend or articulate about 15 degrees or more, about 45 degrees or more, about 60 degrees or more, about 90 degrees or more, about 110 degrees or more, or even about 130 degrees or more. The one or more stylets may have a generally uniform cross section, or the cross section may be variable. At least a portion of the outer surface of the one or more stylets may be substantially the same size as the interior of one or more needle portions of the one or more needles so that the stylet substantially occupies some, most, or all of the interior of the needle. The one or more stylets may be advanced, actuated, or moved from a retracted position to an advanced position. In the retracted position, the distal end of the one or more stylets may be offset or retracted from the distal end of the one or more needles so that a sample storage area is created between the distal end of the stylet, sealing member, or both and the distal end or needle tip of the needle. In the advanced position, the distal end of the one or more stylets, sealing members, or both may be substantially aligned with the distal end of the one or more needles to form a substantially continuous surface or edge. When the needle and stylet extend beyond a distal end of the catheter, the needle can penetrate and separate tissue without coring, ripping, or damaging the tissue. The one or more stylets may include one or more notched portions, recesses, cut-outs, or grooves. The one or more notched portions, recesses, cut-outs, or grooves may be located at a distal end, or at a location between the distal and proximal ends of the stylet. The one or more sealing members may be attached or in communication with the one or more notched portions, recesses, cut-outs, or grooves on the stylet. The one or more stylets may be at least partially withdrawn from the one or more needles to create and/or form a local vacuum at the distal end or needle tip of the needle, in the sample storage area, or both. The one or more stylets may be at least partly withdrawn or completely withdrawn from the needle so that an ancillary vacuum device (i.e., a syringe, a vacuum, a generator, etc.) can effetely draw vacuum from the distal end of the needle. The one or more stylets may be attached to, or in communication with, one or more sealing members so that when the stylet, the sealing member, or both are at least partially moved, a local vacuum can be created or formed at a distal end of the needle.

The one or more sealing members may function to form or provide a local vacuum in the one or more needles. The one or more sealing members may function to create a local vacuum at a distal end of the needle, the needle tip, in the sample storage area, or a combination thereof. The one or more sealing members may function to create a local vacuum at a distal end of the one or more needles, the one or more sample storage areas, or both when moved or translated proximally, distally, or both. The one or more sealing members may function to create a local vacuum at a distal end of the one or more needles without requiring, attaching, or connecting an auxiliary or ancillary device, generator, suction or vacuum device, or a combination thereof. The local vacuum may function independently of the one or more vacuum or suction devices that may be attached to proximal end of the needle, bronchoscope, catheter, or a combination thereof. The one or more sealing members may function to prevent one or more tissue samples, foreign materials, or both from being aspirated or drawn deep into the one or more needles. The one or more sealing members may function to restrict or prevent one or more tissue samples, foreign materials, or both from being drawn or aspirated past the sealing member, while allowing one or more fluids, such as blood, water, irrigation fluid, air, vacuum, suction, the like, or a combination thereof to be aspirated past the sealing member. The one or more sealing members may frictionally engage the one or more tissue samples so that the one or more tissue samples are retained in the sample storage area. The one or more sealing members may function as a space filler to position and/or maintain an undersized stylet in the needle, and/or one or more needle portions. The one or more sealing members may function to prevent tissue samples from moving past the stylet. The one or more sealing members may function to center or align a stylet within the needle, one or more needle portions, or both. The one or more sealing members may function to eject or expel tissue samples from the needle, the sample storage area, or both. The one or more sealing members may be connected to, or in communication with the stylet, to an interior portion of the needle (i.e., an inner diameter or wall), an interior of one or more needle portions, or a combination thereof.

The one or more sealing members may be at least partially deformable, collapsible, expandable, pliable, stretchable, or a combination thereof. The one or more sealing members may occupy some, most, or all of an interior portion of the one or more needles, one or more needle portions, or both. The one or more sealing members may be at least partially rigid and at least partially resist deformation. The one or more sealing members may be stretchable so that when the stylet is moved towards the distal end of the needle, the stylet moves, stretches, deforms, and at least partially displaces the sealing member. The one or more sealing members may fill some, most, or all of an interior of the one or more needles or hypotubes. The one or more sealing members may be a deformable membrane, a rigid or deformable piston, a foamy or spongy member, or a combination thereof. The one or more sealing members may be a silicon or rubber membrane. The one or more sealing members may be fabricated from a rubber, plastic, TPU, or a combination thereof. The one or more sealing members, membranes, or both may expand circumferentially when the stylet is moved, pulled, or retracted in a proximal direction, and may fold downwardly when the stylet is moved or pushed in a distal direction. The one or more sealing members may be a disk. The one or more sealing members may be one or more sealing members that may extend from an interior portion of the needle, the shaft, a first needle portion, a second needle portion, or a combination thereof. The one or more sealing members may be toroidal shaped elements, members, disks, or fingers connected to an interior portion of the needle. The one or more sealing members may be generally u-shaped, circular, oval, or a combination thereof. The one or more sealing members may extend from an interior of the needle and deform around and/or conform to the stylet. The one or more sealing members may deform around the aspirated sample tissue to increase friction to assist in retaining the sample tissue within the needle, the sample storage area, or both while the needle is moved towards and away from the region of interest. The one or more sealing members may include a distal edge that substantially conforms to a distal end or needle tip of the needle. The one or more sealing members may include a distal edge or surface that is angled, beveled, flat, and irregular, rounded, the like, or a combination thereof. The one or more sealing members may include a body and one or more extensions projecting from the body. The one or more extensions may be deformable, bendable, foldable, compressible, displaceable, and/or adaptable to an interior of the needle so that some, most, or all of the interior of the needle is occupied. The one or more extensions may fold distally, proximally, circumferentially, irregularly, or a combination thereof. The one or more extensions may collapse, bend, deform, move, the like or a combination thereof so that the stylet can be moved within the needle, within different portions or gauges of a needle (i.e., from a larger gauge to a smaller gauge, or vice versa) while still occupying some, most or all of the interior of the needle. The one or more sealing members may deform and/or comply simultaneously to two or more interior sizes of the needle. The one or more sealing members may be restricted or prevented from being withdrawn from the needle. The one or more sealing members may be fixedly connected to an interior of the needle, to one or more portion of the needle, or both. The one or more sealing members may include a cross section or size that is substantially the same size as a first portion of the needle, but larger than another portion of the needle, so that the sealing member is restricted from being drawn into the another portion of the needle, or restricted from being withdraws from the needle. The one or more sealing members may comprise two portions (i.e., a first or upper portion and a second or lower portion). The one or more sealing members, the first portion, the second portion, or a combination thereof may be pulled or moved proximally und in doing so, one of the portions (i.e., either the first portion or the second portion) is moved further than the other portion so that a gap or opening is provided therebetween. The one or more sealing members may prevent tissue samples from moving past the sealing member(s), but the gap or opening may allow one or more fluids (i.e., blood, air, vacuum, suction, irrigation fluid, etc.) to move past the sealing member through the gap or opening. The sealing member may include one or more portions that include a cytology brush, a collapsible basket, a grasping forceps, the like or a commination thereof. The cytology brush, the collapsible basket, the grasping forceps, the like or a commination thereof may provide a local vacuum when moved proximally relative to the distal end of the needle. The cytology brush, the collapsible basket, the grasping forceps, the like or a commination thereof may restrict or prevent tissue samples from aspirating past the sealing member. The one or more sealing members may be a spring plunger. The one or more sealing members may include an outer-coiled region and an inner-coiled region in communication with the stylet. When the stylet is pulled proximally, the inner-coiled region meets the outer-coded region, which creates the local vacuum at a distal end of the needle, in sample storage area, or both. The stylet can be pulled back and forth (i.e., proximally and distally) one or more times to create the local vacuum. That is, the stylet and/or the sealing member can be primed to create the local vacuum. A stop feature or nub may be provided in the interior of the needle to restrict or prevent the sealing member, the outer-coiled region, or both from being pulled past a predetermined point in the needle, or withdrawn from the needle. The stylet, the spring plunger, the sealing member, or a combination thereof can be completely removed from the needle. A duckbill may be provided in the sealing member, the inner coiled region, the outer coiled region, or both which may help vacuum to be pulled through the sealing member, especially when one or more vacuum or suction devices are provided at a proximal end of the needle, the catheter, the bronchoscope, or a combination thereof. The duck bill may create an obstruction so that the obtained tissue sample is restricted or prevented from moving or aspirating beyond the inner coiled region, the outer coiled region, the sealing member, or a combination thereof.

The one of more vacuum or suction devices may function to aspirate one or more tissue samples, foreign matter, or both into the needle. The one or more vacuum or suction devices may function to pull a vacuum along the length of the needle. The one or more vacuum or suction devices may function to pull a negative vacuum along the length of the needle so that collected tissue samples can be expelled from the needle, the sample storage area, or both. The one or more vacuum or suction devices may be a pump, a syringe, a generator, a vacuum pump, a suction pump, the like, or a combination thereof. The one or more vacuum or suction devices may be connected to the needle with one or more valves, Y-connectors, control mechanisms, or a combination thereof. The one or more vacuum or suction devices may be automatically activated when the stylet is at least partially removed from the needle; may be activated when a control is activated by the surgeon, or both. The one or more vacuum or suction devices may function in combination with the local vacuum created at a distal end of the needle, or may function independent of the local vacuum.

FIG. 1 illustrates a system 10 including a bronchoscope 12. A catheter 14 extends from a working channel 16 of the bronchoscope 12, and includes therein a sampling device or needle 100 with a needle tip 107 at a distal end 106 of the needle 100.

Figure 2:
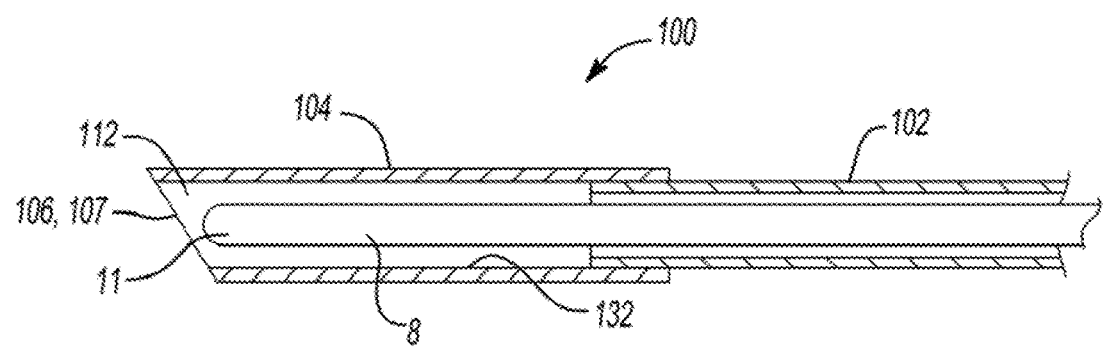
FIG. 2 illustrates a cross-sectional view of a needle and a stylet according to the teachings herein.

FIG. 2 illustrates a portion of a sampling device or needle 100. The needle 100 includes a first portion 102 and a second portion 104. A distal end 106 of the second portion 104 includes a needle tin 107 for cutting, coring, shearing, and/or obtaining tissue from a site or region of interest. A stylet 8, including a distal end 11, is disposed in the interior 132 of the needle 100. Between an outer surface of the stylet 8 and the interior 132 of the needle 100 is a gap 112. The gap 112 also extends between the respective distal ends 106, 11 of the second portion 104 and the stylet 8. Once/as the needle tip 107 cuts, cores, and/or shears tissue from a site or region of interest, a suction source (not illustrated), in communication with a proximal end of the needle 100, can pull or aspirate the cut, cored, and/or sheared tissue samples into the gap 112. The suction source may also pull the tissue samples around the stylet 8 and even into the first portion 102 of the needle 100.

FIGS. 3A and 3B illustrate a portion of an improved stylet 108 for use with the sampling device or needle 100. While the needle 100 was described above as including a first portion 102 and a second portion 104, it is understood that needle 100 may also include a single elongated portion (i.e., only the first portion 102, or the second portion 104). Referring back to the stylet 108, the stylet 108 includes a notched or recessed area 118 and a sealing member 120. The sealing member 120 includes a body 122 and one or more extensions 124 that, in a steady-state configuration (FIG. 3A), extend generally radial relative to a longitudinal axis 116 of the stylet 108. Once the stylet 108 is inserted into the interior 132 of the needle 100, the extensions 124, the body 122, or both are configured to fold, bend, and/or deform (FIG. 3B) and at least partially contact the interior 132 of the needle 100 in a line-to-line configuration, or with a slight interference. That is, once inserted into the needle 100, an overall radial width and/or size of the sealing member 120 and extensions 124 is configured to substantially adapt, conform, and match the interior 132 of the needle 100.

During use, once the needle 100 is in the patient and the needle tip 107 is near the region or site of interest, pulling or retracting the stylet 108 in a first direction 134 creates a sample storage area 114 between the distal end 106 of the needle 100 and a distal end 138 of the sealing member 120. Moreover, pulling, or retracting the stylet 108 in the first direction 134 reduces pressure in the sample storage area 114, which creates a local vacuum at a distal end 106 of the needle 100 and in sample storage area 114. Accordingly, as the needle tip 107 cuts, cores, shears, and/or obtains tissue at the site or region of interest, tissue samples can be aspirated or drawn into the sample storage area 114. Aspiration of tissue samples beyond the sealing member 120 is restricted or prevented from due to the line-to-line or slight interference between the sealing member 120 and the interior 132 of the needle 100. Once the needle 100 is removed from the patient, the stylet 108 can be advanced in the second direction 136 so that the distal surface 138 of the sealing member 120 can easily expel the tissue samples from the needle 100.

FIG. 4A illustrates a portion of a sampling device or needle 100. A distal end 106 of the needle 100 includes a needle tip 107 for cutting, coring, shearing, and or obtaining tissue from a site or region of interest. A stylet 108 is disposed in the interior 132 of the needle 100. The stylet 108 includes a sealing member 120 with a width or size that is substantially the same as the interior 132 of the needle 100. That is, the sealing member 120 is adapted to match the interior 132 of the needle 100. A distal end 138 of the sealing member 120 is substantially aligned with the distal end 106 of the needle 100 so that during use. The sealing member 120 can block or prevent debris (i.e., tissue, blood, and the like) from entering the needle 100 as the needle 100 is advanced towards the site or region of interest.

FIGS. 4B and 4C illustrate the stylet 108 at least partially pulled or retracted in the first direction 134 thereby creating a sample storage area 114 between the respective distal ends 106, 138 of the needle 100 and the sealing member 120. Moreover, pulling or retracting the stylet 108 in the first direction 134 reduces pressure in the sample storage area 114, which creates a local vacuum V at a distal end 106 of the needle 100 and in sample storage area 114. Accordingly, as the needle tip 107 cuts, cores, shears, and/or obtains tissue at the site or region of interest, tissue samples T can be aspirated or drawn into the sample storage area 114. Aspiration of tissue samples T beyond the sealing member 120 is restricted or prevented due to the line-to-line or slight interference between the sealing member 120 and the interior 132 of the needle 100. Once the needle 100 is removed from the patient, the stylet 108 can be advanced in the second direction 136 so that the distal surface 138 of the sealing member 120 can easily expel the tissue samples T from the sample storage area 114.

FIG. 5 illustrates a portion of a sampling device or needle 100. The needle 100 includes a first portion 102 and a second portion 104. A distal end 106 of the needle 100 includes a needle tip 107 for cutting, coring, shearing, and/or obtaining tissue from a site or region of interest. A stylet 108 is disposed within the interior 132 of the needle 100. The stylet 108 includes a sealing member 120 with a width or size that is substantially the same as the interior 132 of the needle 100. That is, as the stylet 108 is moved in either a first direction 134 and a second direction 136, the sealing member 120 is adapted to match the interior 132 of the needle 100 at the first portion 102 and the second portion 104. During use, the stylet 108 pulled or retracted in the first direction 134 to create a sample storage area 114 between the respective distal ends 106, 138 of the needle 100 and the sealing member 120. Moreover, pulling or retracting the stylet 108 in the first direction 134 reduces pressure in the sample storage area 114, which creates a local vacuum at a distal end 106 of the needle 100 and in sample storage area 114. Accordingly, as the needle tip 107 cuts, cores, shears, and/or obtains tissue at the site or region of interest, pulling or retracting the stylet 108 in the first direction 134 causes tissue samples to aspirated or drawn into the sample storage area 114. Aspiration of tissue samples beyond the sealing member 120 is restricted or prevented due to the line-to-line or slight interference between the sealing member 120 and the interior 132 of the needle 100. Once the needle 100 is removed from the patient the stylet 108 can be advanced in the second direction 136 so that the distal surface 138 of the sealing member 120 can easily expel the tissue samples from the sample storage area 114.

FIG. 6 illustrates a portion of a sampling device or needle 100. The needle 100 includes a first portion 102 and a second portion 104. A distal end 106 of the needle 100 includes a needle tip 107 for cutting, coring, shearing, and/or obtaining tissue from a site or region of interest. A stylet 108 is disposed in the interior 132 of the needle 100. The stylet 108 includes a sealing member 120 and a second sealing member 120', each of which have a width or size that is substantially the same as the interior 132 of the needle 100. That is, the sealing member 120 has a width or size that is substantially the same as the interior 132 of the second portion 104, and the second sealing member 120' has a width or size that is substantially the same as the interior 132 of the first portion 102. One or both of the sealing members 120, 120' may also adapt to the size of the other respective portion 102, 104. That is, if/when the stylet 108 is moved in the first direction 134, the sealing member 120 may adapt to the interior 132 of the first portion 102. Moreover, if when the stylet 108 is moved in the second direction 136, the second sealing member 120' may adapt to the interior 132 of the first portion 102. During use, the stylet 108 can be pulled or retracted in the first direction 134 to create a sample storage area 114 between the respective distal ends 106, 138 of the needle 100 and the sealing member 120. Moreover, pulling or retracting the stylet 108 in the first direction 134 reduces pressure in the sample storage area 114, which creates a local vacuum at a distal end 106 of the needle 100 and in sample storage area 114. Accordingly, as the needle tip 107 cuts, cores, shears, and/or obtains tissue at the site or region of interest, tissue samples can be aspirated or drawn into the sample storage area 114 by pulling or retracting the stylet 108 in the first direction 134. Aspiration of tissue samples beyond the sealing member 120 is restricted or prevented due to the line-to-line or slight interference between the sealing member 120 and the interior 132 of the needle 100. Once the needle 100 is removed from the patient, the stylet 108 can be advanced in the second direction 136 so that the distal surface 138 of the sealing member 120 can easily expel the tissue samples from the sample storage area 114.

FIG. 7A illustrates a portion of a sampling device or needle 100. A distal end 106 of the needle 100 includes a needle tip 107 for cutting, coring, shearing, and/or obtaining tissue from a site or region of interest. A stylet 108, including a distal end 110, is disposed within the interior 132 of the needle 100. A sealing member 120 is disposed in the interior 132 of the needle 100. The sealing member 120 may be connected to the interior 132 of the needle 100, the distal end 110 of the stylet, or both. A sample storage area 114 is defined between the sealing member 120 and the distal end 106 of the needle 100.

FIG. 7B illustrates the stylet 108 that is pulled or retracted in the first direction 134, which draws the sealing member 120 proximally and reduces pressure in the sample storage area 114. Accordingly, a local vacuum is created at a distal end 106 of the needle 100 and in sample storage area 114. During use, as the needle tip 107 cuts, cores, and/or shears tissue at the site or region of interest, tissue samples can be aspirated or drawn into the sample storage area 114 by pulling or retracting the stylet 108 in the first direction 134. Aspiration of tissue samples beyond the sealing member 120 is restricted or prevented due to the line-to-line or slight interference between the sealing member 120 and the interior 132 of the needle 100.

FIG. 7C illustrates the stylet 108 moved or advanced in the second direction 136. Once the needle 100 is removed from the patient, the stylet 108 can be advanced in the second direction 136 so that the sealing member 120 moves and stretches so that the tissue samples to can be easily expelled from the sample storage area 114. Moreover, during advancement of the needle 100 towards the site or region of interest, distal alignment of the stylet 108 and needle 100 can block or prevent debris (i.e., tissue, blood, and the like) from prematurely entering the sample storage area 114.

Figure 8:
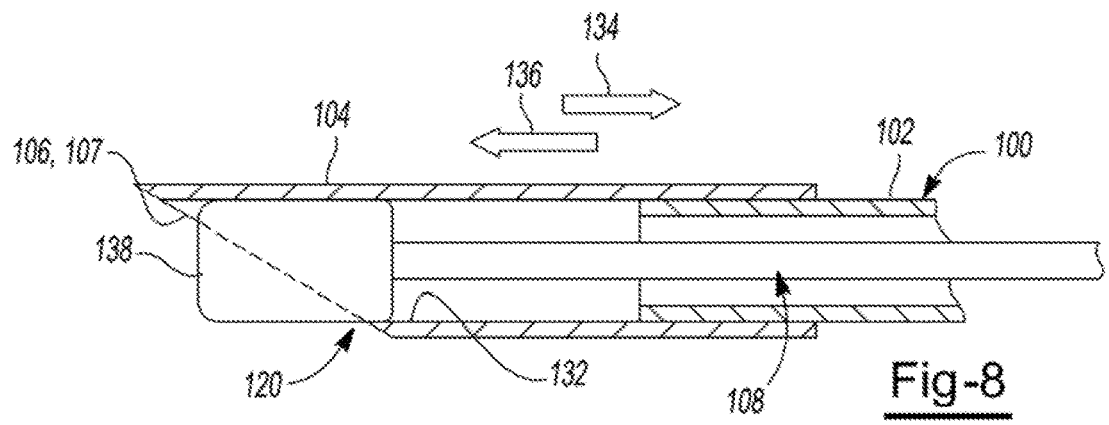
FIG. 8 illustrates a cross-sectional view of a needle, a stylet, and a sealing member according to the teachings herein.

FIG. 8 illustrates a portion of a sampling device or needle 100. The needle 100 includes a first portion 102 and a second portion 104. A distal end 106 of the needle 100 includes a needle tip 107 for cutting, coring, shearing, and/or obtaining tissue from a site or region of interest. A stylet 108 is disposed within the interior 132 of the needle 100. The stylet 108 includes a sealing member 120 with a width or size that is substantially the same as the interior 132 of the needle 100. That is the sealing member 120 is adapted to match the interior 132 of the second portion 104. A distal end 138 of the sealing member 120 can be substantially aligned with the distal end 106 of the needle 100 so that during needle 100 advancement towards the site or region of interest, the sealing member 120 can block or present debris (i.e., tissue, blood, and the like) from entering the needle 100.

When the stylet 108 is pulled or retracted in the first direction 134, a sample storage area 114 is created between the respective distal ends 106, 138 of the needle 100 and the sealing member 120. Moreover, pulling or retracting the stylet 108 in the first direction 134 reduces pressure in the sample storage area, which creates a local vacuum at a distal end 106 of the needle 100 and in sample storage area 114. Accordingly, as the needle tip 107 cuts, cores, shears, and/or obtains tissue at the site or region of interest, tissue samples can be aspirated or drawn into the sample storage area 144 by pulling or retracting the stylet 108 in the first direction 134. Aspiration of tissue samples beyond the sealing member 120 is restricted or prevented due to the line-to-line or slight interference between the sealing member 120 and the interior 132 of the needle 100. Once the needle 100 is removed from the patient, the stylet 108 can be advanced in the second direction 136 so that the distal surface 138 of the sealing member 120 can easily expel the tissue samples from the sample storage area.

Figure 9A:
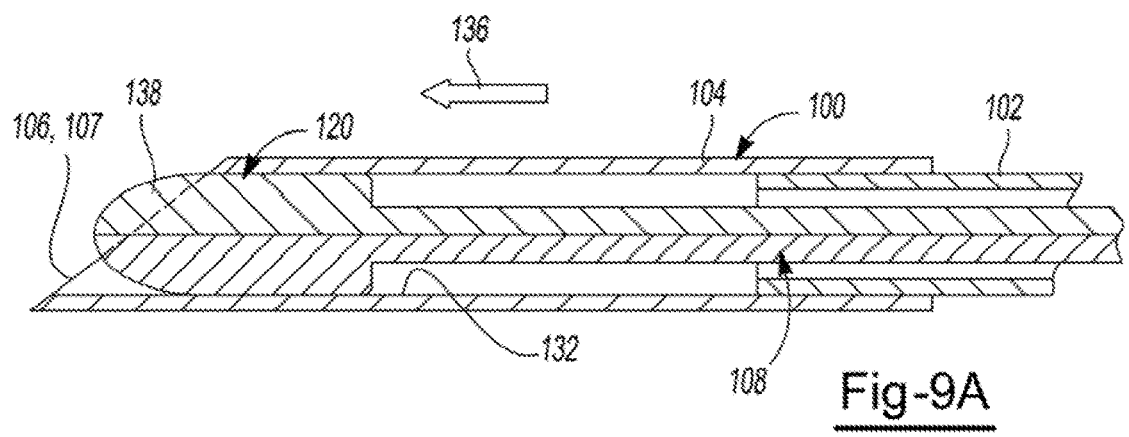
FIG. 9A illustrates a cross-sectional view of a needle, a stylet, and a sealing member according to the teachings herein.

FIG. 9A illustrates a portion of a sampling device or needle 100. The needle 100 includes a first portion 102 and a second portion 104. A distal end 106 of the needle 100 includes a needle tip 107 for cutting, coring, shearing, and/or obtaining tissue from a site or region of interest. A stylet 108 is disposed within the interior 132 of the needle 100. The stylet 108 includes a sealing member 120 with a width or size that is substantially the same as the interior 132 of the needle 100. That is, the sealing member 120 is adapted to match the interior 132 of the second portion 104. A distal end 138 of the sealing member 120 can be substantially aligned with the distal end 106 of the needle 100 so that during needle 100 advancement towards the site or region of interest, the sealing member 120 can block or prevent debris (i.e., tissue, blood, and the like) from entering the needle 100.

Figure 9B:
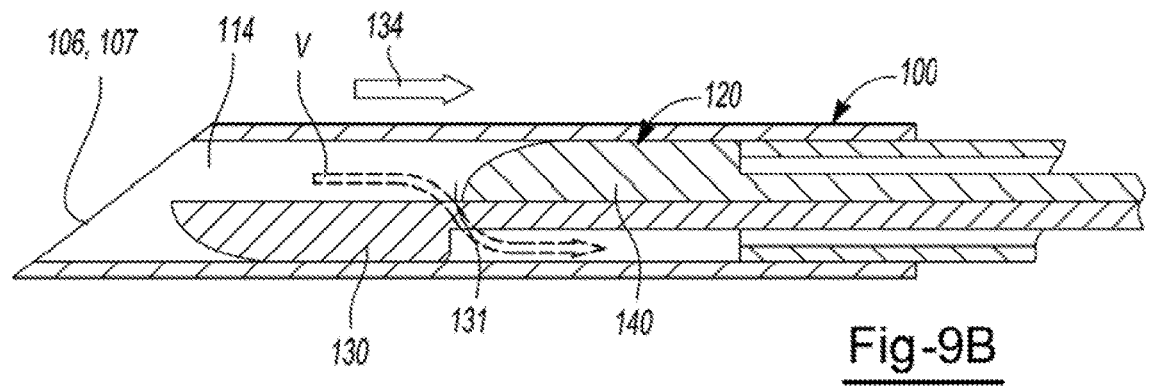
FIG. 9B illustrates a cross-sectional view of a needle, a stylet, and a sealing member according to the teachings herein.

FIG. 9B illustrates a portion of a sampling device or needle 100. When the stylet 108 is pulled or retracted in the first direction 134, a sample storage area 114 is created between the respective distal ends 106, 138 of the needle 100 and the sealing member 120. When both sealing portions 130 and 140 are pulled proximally in direction 134 simultaneously, the close fit between the stylet, and the needle creates a seal and acts as a plunger piston to create a local vacuum. Moreover, pulling or remitting the stylet 108 in the first direction 134 reduces pressure in the sample storage area 114, which creates a local vacuum V at a distal end 106 of the needle 100 and in sample storage area 114. When the stylet 108 is pulled or retracted in the first direction 134, a first sealing portion 140 of the sealing member 120 may also separate from a second sealing portion 130 of the sealing member 120 to create a gap 131 therebetween. When the two stylet halves 130 and 140 are separated, the gap 131 opens and allows a fluid path from the distal opening of the needle to the proximal end where a syringe would provide suction. This arrangement would allow the physician the option of pulling a local vacuum or a more traditional vacuum with a syringe while the stylet provides better occlusion of the needle due to the close fit to the distal needle section 104. Accordingly, as the needle tip 107 cuts, cores, shears, and/or obtains tissue at the site or region of interest, tissue samples can be aspirated or drawn into the sample storage area 114. Aspiration of tissue samples beyond the sealing member 120 is restricted or prevented due to the line-to-line or slight interference between the sealing member 120 and the interior 132 of the needle 100. Moreover, the gap 131 between the first and second sealing portions 130, 140 can be dimensioned and/or a filtration system may be provided so that tissue samples are restricted from being aspirated or drawn there through, however other fluids (i.e., air, blood, etc.) can pass through the gap 131. Once the needle 100 is removed from the patient, the stylet 108 can be advanced in the second direction 136 so that the distal surface 138 of the sealing member 120 can easily expel the tissue samples from the sample storage area 114.

Figure 10A:
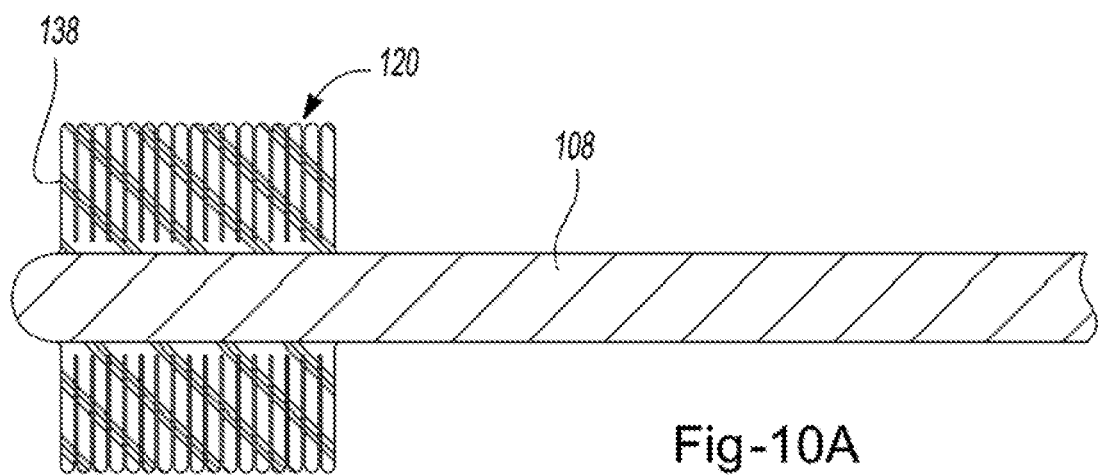
FIG. 10A illustrates a cross-sectional view of a stylet and a sealing member for use with a needle according to the teachings herein.
Figure 10B:
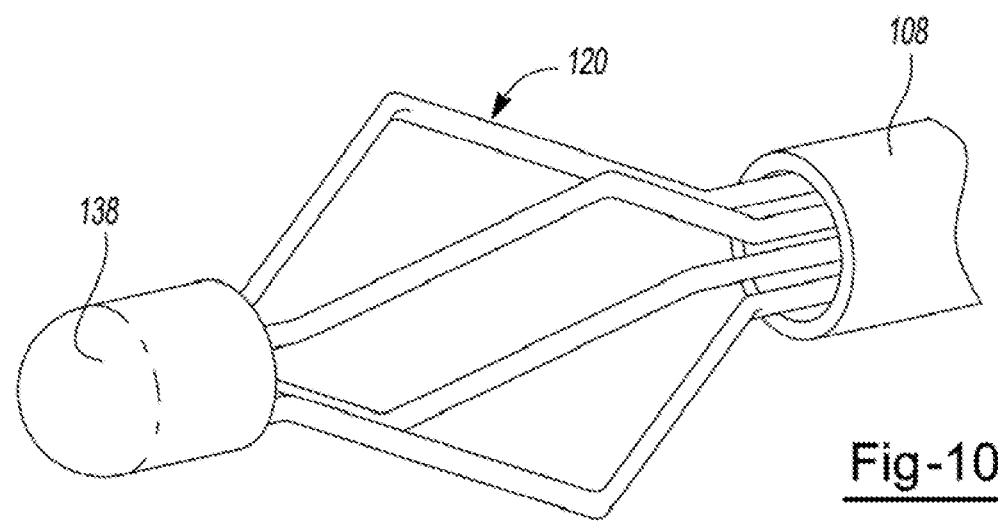
FIG. 10B illustrates a cross-sectional view of a stylet and a sealing member for use with a needle according to the teachings herein.
Figure 10C:
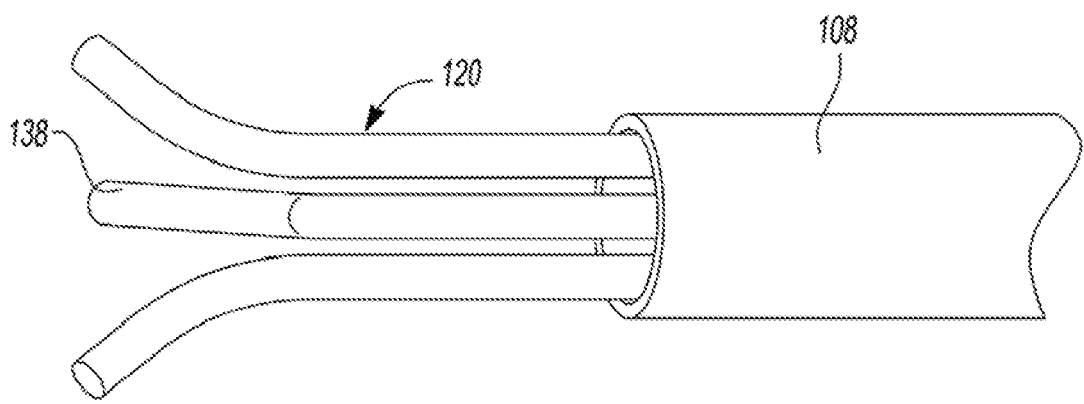
FIG. 10C illustrates a cross-sectional view of a stylet and a sealing member for use with a needle according to the teachings herein.

FIGS. 10A, 10B, and 10C illustrate additional configurations of the sealing member 120 for use with any of the aforementioned stylets 108 and sampling devices or needles. The sealing member 130 can be adapted to conform to and match the interior of the needle. A distal end 138 of the sealing member 120 is substantially aligned with the distal end of the needle (not illustrated) so that during use, the sealing member 120 can block or present debris (i.e., tissue, blood, and the like) from entering the needle during needle advancement towards the site or region of interest. The sealing member 120 may be or resemble a cytology brush (FIG. 10A), a collapsible basket (FIG. 10B), and grasping forceps (FIG. 10C). When the stylet 108 is pulled or retracted in a first direction, a sample storage area is created between the respective distal ends of the needle and the sealing member 120. Moreover, pulling or retracting the stylet 108 in the first direction reduces pressure in the sample storage area, which creates a local vacuum V in sample storage area. Accordingly, as the needle tip cuts, cores, shears, and/or obtains tissue at the site or region of interest, tissue samples can be aspirated or drawn into the sample storage area 114. Some of the tissue samples can also be aspirated against the cytology brush (FIG. 10A), and/or into the basket (FIG. 10B) or the forceps (FIG. 10C), which are expanded when the stylet 108 is moved in the second direction. Aspiration of tissue samples beyond the sealing member 120 is restricted or prevented due to the line-to-line or slight interference between the sealing member 120 and the interior 132 of the needle 100. Once the needle 100 is removed from the patient, the stylet 108 can be advanced in a second direction so that the distal surface 138 of the sealing member 120 can easily expel the tissue samples from the sample storage area.

FIG. 11 illustrates a portion of a sampling device or needle 100. A distal end 106 of the needle 100 includes a needle tip 107 for cutting, coring, shearing, and/or obtaining tissue from a site or region of interest. A stylet 108 is disposed within the interior of the needle 100. The stylet 108 may include a sealing member 120 with a width or size that is substantially the same as the interior of the needle 100. A control mechanism 142, including a first port 144 and a second port 146 is located at proximal end of the needle 100. A suction device 148, such as a syringe, may be connected to the first port 144, while the second port 146 provides a passage for the stylet 108 to be pulled in the first direction 134. Suction device 148 may provide additional pressure as an alternative to or in addition to that created by the different local vacuum mechanisms described herein. A seal 150 is located in the second port 146.

During use, the stylet 108 is pulled, or retracted in the first direction 134 to create a sample storage area between the respective distal ends of the needle 100 and the sealing member 120. Moreover, pulling or retracting the stylet 108 in the first direction 134 reduces pressure in the sample storage area, which creates a local vacuum at a distal end 106 of the needle 100 and in sample storage area. Accordingly, as the needle tip 107 cuts, cores, shears, and or obtains tissue at the site or region of interest, tissue samples can be aspirated or drawn into the sample storage area 114. Aspiration of tissue samples beyond the sealing member 120 is restricted or prevented due to the line-to-line or slight interference between the sealing member 120 and the interior 132 of the needle 100. Once the needle 100 is removed from the patient, the stylet 108 can be advanced in the second direction 136 so that the distal surface 138 of the sealing member 120 can easily expel the tissue samples from the sample storage area 114. It is contemplated that this embodiment can be combined with any of the other embodiments to provide the option of having additional suction pressure provided at a proximal end of the device in addition to the creation of a local vacuum to enhance the function of the device at the distal end as needed.

In addition, or as an alternative to pulling or retracting the stylet 108 in the first direction 134, the suction device 148 may be applied to create a local vacuum at a distal end 100 of the needle 100 and in sample storage area. In this regard, as the stylet 108 is withdrawn in the first direction 134 to create the sample storage area, the suction device 148 can be activated automatically, or via one or more controls. The seal 150 prevents vacuum or suction loss between the second port 146 and the stylet 108.

Figure 12B:
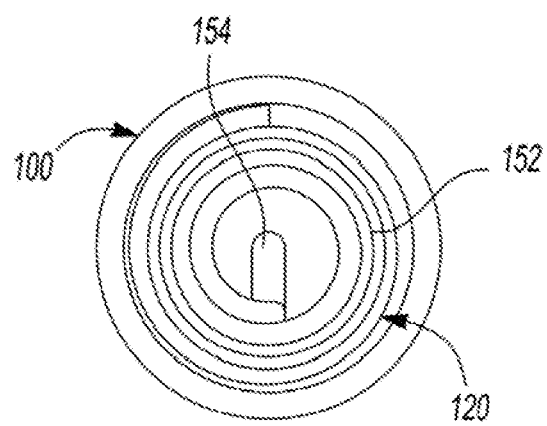
FIG. 12B illustrates a front view of a sealing member for use with a needle and stylet according to the teachings herein.

FIGS. 12A and 12B illustrate a portion of a sampling device or needle 100. The needle 100 includes a first portion 102 and a second portion 104. A distal end 106 of the needle 100 includes a needle tip 107 for cutting, coring, shearing, and/or obtaining tissue from a site or region of interest. A stylet 108 is disposed within the interior 132 of the needle 100. The stylet 108 includes a sealing member 120 with a width or size that is substantially the same as the interior 132 of the needle 100. The sealing member 120 may be a spring plunger that includes an outer-coiled region 152 and an inner-coiled region 154. It is also contemplated that the sealing member 120 may be a spring plunger that includes a single coiled region. During use, the stylet 108 is pulled or retracted in the first direction 134 to create a sample storage area 114 between the respective distal ends of the needle 100 and the sealing member 120. Moreover, pulling or retracting the stylet 108 in the first direction 134 reduces pressure in the sample storage area 114, which creates a local vacuum at a distal end 106 of the needle 100 and in sample storage area 114. More specifically, when the stylet 108 is pulled in the first direction 134, the inner-coiled region 154 meets the outer-coiled region 152, which creates the local vacuum at a distal end 106 of the needle 100 and in sample storage area 114. A stop (not illustrated) may be provided in the interior 132 of the needle 100 to restrict or prevent the sealing member 120, the outer coiled region 152 from being pulled past a predetermined point in the needle 100. Accordingly, as the needle tip 107 cuts, cores, shears, and/or obtains tissue at the site or region of interest, tissue samples can be aspirated or drawn into the sample storage area 114. Aspiration of tissue samples beyond the sealing member 120 is restricted or prevented due to the line-to-line or slight interference between the larger outer-coiled region 152 and the interior 132 of the needle 100. Once the needle 100 is removed from the patient, the stylet 108 can be advanced in the second direction 136 so that the sealing member 120 can easily expel the tissue samples from the sample storage area 114.

Figure 13A:
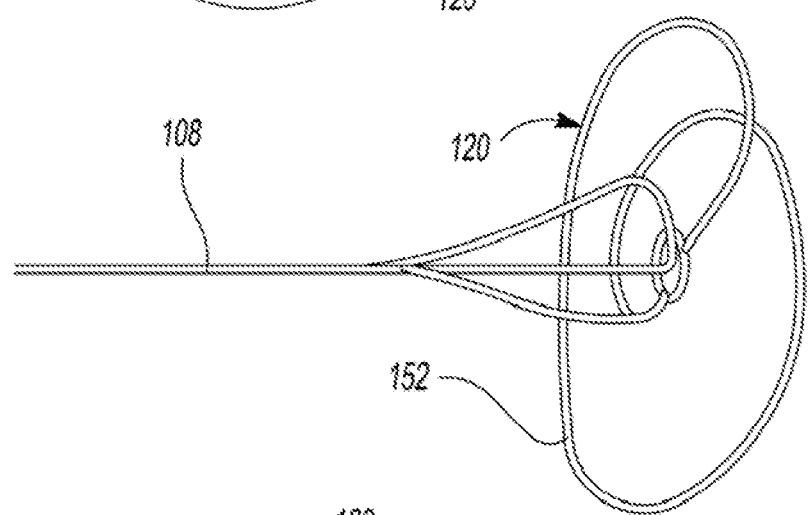
FIG. 13A illustrates a side view of a stylet and a sealing member for use with a needle according to the teachings herein.
Figure 13B:
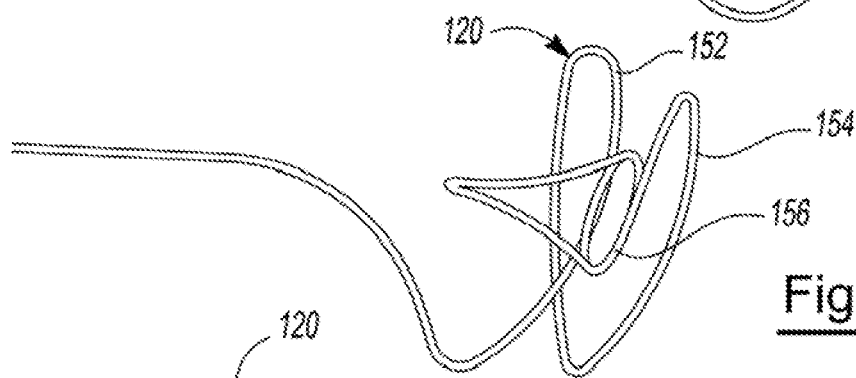
FIG. 13B illustrates a side view of a stylet and a sealing member for use with a needle according to the teachings herein.
Figure 13C:
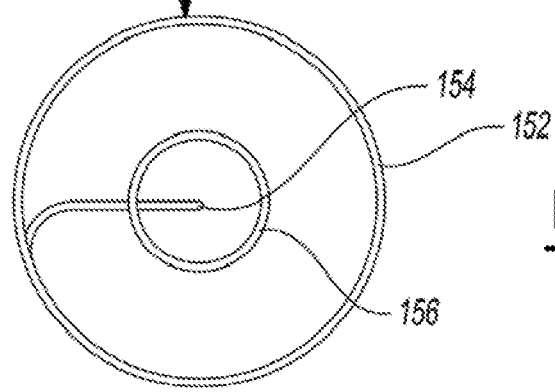
FIG. 13C illustrates a front view of a sealing member for use with a needle and stylet according to the teachings herein.

FIGS. 13A, 13B, and 13C illustrate additional configurations of the sealing member 120 for use with any of the aforementioned stylets 108 and needles. The sealing member 120 can be adapted to conform to and match the interior of the needle. The sealing member 120 includes an outer-coiled region 152, an inner coiled region 154, and a duck bill 156. A control mechanism (not illustrated), including a first port and a second port is located at proximal end of the needle. A suction device (like suction device 148, not illustrated), such as a syringe, may be connected to the first port of the control mechanism, while the second port provides a passage for the stylet 108 to be pulled in a first direction. Suction device 148 may provide additional pressure as an alternative to or in addition to that created by the local vacuum mechanism. During use, the stylet 108 pulled or retracted in the first direction 134 to create a sample storage area 114 between the respective distal ends of the needle 100 and the sealing member 120. Moreover, pulling or retracting the stylet 108 in the first direction 134 reduces pressure in the sample storage area 114, which creates a local vacuum at a distal end 106 of the needle and in sample storage area. More specifically, when the stylet 108 is pulled in the first direction 134, the inner-coiled region 154 meets the outer-coiled region 152, which creates the local vacuum at a distal end 106 of the needle 100 and in sample storage area 114. A stop (not illustrated) may be provided in the interior of the needle to restrict or prevent the sealing member 120 from being pulled past a predetermined point in the needle. When the stylet 108 is pulled or retracted in a first direction, a sample storage area is created between the respective distal ends of the needle and the sealing member 120. Moreover, pulling or retracting the stylet 108 in the first direction reduces pressure in the sample storage area, which creates a local vacuum in sample storage area. Accordingly, as the needle tip cuts, cores, shears, and/or obtains tissue at the site or region of interest, tissue samples van be aspirated or drawn into the sample storage area. Aspiration of tissue samples beyond the sealing member 120 is restricted or prevented due to the line-to-line or slight interference between the sealing member 120 and the interior of the needle. Once the needle is removed from the patient, the stylet 108 can be advanced in a second direction so that the sealing member 120 can easily expel the tissue samples from the sample storage area.

In addition, or as an alternative to pulling or retracting the stylet 108 in the first direction, the suction device can be applied to create a local vacuum at a distal end of the needle and in sample storage area. In this regard, as the stylet 108 is moved in the first direction to create the sample storage area, the suction device can be activated automatically, or via one or more controls. The duck bill 156 helps vacuum flow through the sealing member 120 when the suction device is applied at the proximal end of the needle.

It is contemplated that the duck bill valve 156 may be used as a pump. A user may pump the stylet 108 back and forth pulling the sample into the sample storage area. The local vacuum created and the ability to collect and retain a sample is magnified on each pump.

Figure 14A:
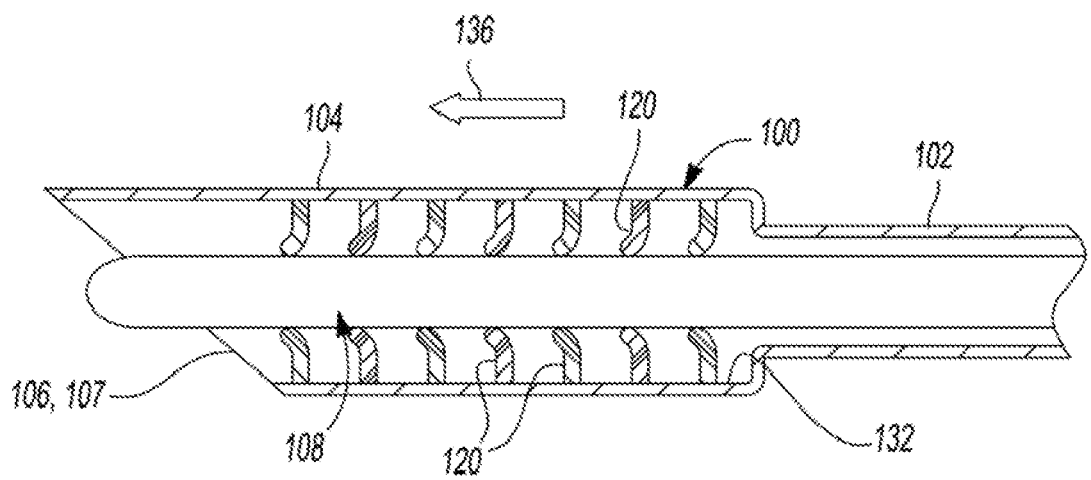
FIG. 14A illustrates cross-sectional view of a needle, a stylet, and a sealing member according to the teachings herein.

FIG. 14A illustrates a portion of a sampling device or needle 100. The needle 100 includes a first portion 102 and a second portion 104. A distal end 106 of the needle 100 includes a needle tip 107 for cutting, coring, shearing, and/or obtaining tissue from a site or region of interest. A stylet 108 is disposed within the interior 132 of the needle 100. A plurality of sealing members 120 extend from the interior 132 of the second portion 104. The sealing members 120 are configured to flex and deform about the stylet 108 so that the sealing members 120 at least partially contact the stylet 108. At least some of the sealing members 120 (i.e., at a distal portion of the second portion 104) can block or prevent debris (i.e., tissue, blood, and the like) from entering the needle 100 during needle 100 advancement towards the site or region of interest. Contact between the sealing members 120 and the stylet 108 also blocks or prevent debris from entering the needle 100 during needle 100 advancement. Contact between the sealing members 120 and the stylet 108 also substantially centers the stylet 108 in the needle 100.

Figure 14B:
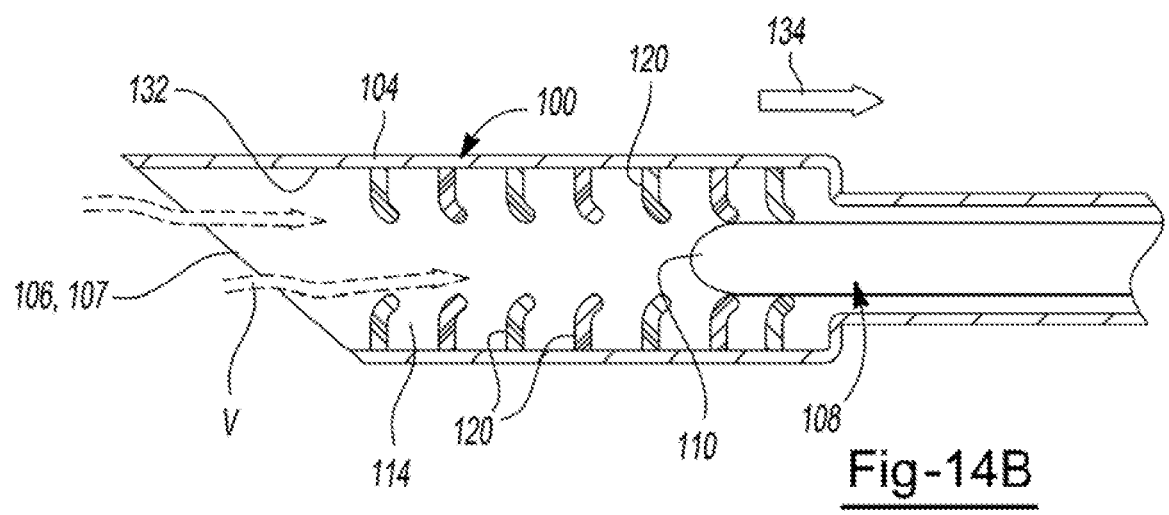
FIG. 14B illustrates a cross-sectional view of a needle, a stylet, and a sealing member according to the teachings herein.

FIG. 14B illustrates a portion of a sampling device or needle 100. When the stylet 108 is pulled or retracted in the first direction 134, a sample storage area 114 is created between the respective distal ends 106, 110 of the needle 100 and the stylet 108. Moreover, pulling or retracting the stylet 108 in the first direction 134 reduces pressure in the sample storage area 114, which creates a local vacuum V at a distal end 106 of the needle 100 and in sample storage area 114. Accordingly, as the needle tip 107 cuts, cores, shears, and/or obtains tissue at the site or region of interest, the tissue samples can be aspirated or drawn into the sample storage area 114. The seating members 120 can block and at least partially deform around the tissue samples so that aspiration of tissue samples beyond the sample storage area 114 and the stylet 108 is restricted or prevented. Once the needle 100 is removed from the patient, the stylet 108 can be advanced in the second direction 136 so that the stylet 120 can easily expel the tissue samples from the sample storage area 114.

With reference to the aforementioned figures, a method for obtaining tissue samples from a site or region of interest will be described. The bronchoscope 12 can be inserted into a location in a patient's lung through the patient's mouth. A TBNA device, which generally includes a catheter 14, a needle 100 disposed within the catheter 14, and a stylet 108, can be inserted through a working channel 16 of the bronchoscope 12 and directed towards a lymph node. The stylet 108 can be disposed in the needle 100 such that the distal ends 110, 106 of the stylet 108 and the needle 100 are substantially aligned. Accordingly, the stylet 108 can block or prevent debris (i.e., tissue, blood, and the like) from, entering the needle 100 as the TBNA device is advanced towards the lymph node.

Once the TBNA device is near the lymph node, the stylet 100 can be proximally moved from the needle 100 so that space for collecting tissue samples T is created within the needle 100 (i.e., a sample storage area 114). The needle 100 is then advanced towards the lymph node so that a needle tip 107 can penetrate, cut, core, and/or shear tissue from the lymph node for sampling. The needle 100 can be reciprocated so that the needle tip 107 collects a sufficient tissue sample T. The cut, cored, and/or sheared tissue samples T are then aspirated into the sample storage area 114 via the local vacuum V created at the distal end 106 of the needle 100 and in the sample storage area 114. That is, the local vacuum V is created by moving the stylet 108 and the sealing member 120 proximally away from the distal end 106 of the needle 100. Because the sealing member 120 occupies some, most, or all of the interior 132 of the needle 100, moving the sealing member 120 proximally creates the local vacuum V at the distal end 106 of the needle 100 and in the sample storage area 144. A distal surface 138 of the sealing member 120 may restrict or prevent the tissue sample T from aspirating past the sealing member 120; however, the sealing member 120 may at least partially deform or split so that fluids such as blood, irrigation fluid, air, vacuum, etc., can be aspirated past the sealing member 120. Once a sufficient tissue sample T has been collected, the TBNA device can be removed from the bronchoscope 12. Once removed, the stylet 108, the sealing member 120, or both can be moved distally so that the distal surface 138 of the sealing member 120 can move or push the collected tissue sample T distally and out of the needle 100. Alternatively, or in addition, air may be forced through needle 100 via an ancillary device so that the sample tissue T can be expelled from the sample storage area 114 and evaluated.

Any numerical values recited herein include all values from the lower value to the upper value in increments of one unit provided that, there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The omission in the following claims of any aspect of subject matter that is disclosed herein is not a disclaimer of such subject matter, nor should it be regarded that the inventors did not consider such subject matter to be part of the disclosed inventive subject matter.

LISTING OF REFERENCE NUMERALS

V local vacuum
T sample tissue
D1 interior of first portion 102
D2 interior of second portion 104
10 system
12 bronchoscope
14 catheter
8 stylet
100 sampling device or needle
102 first portion (of needle 100)
104 second portion (of needle 100)
106 distal end (of second portion 104)
107 needle tip (of second portion 104; of needle 100)
108 stylet
110 distal end (of stylet 108)
112 gap;
114 sample storage area
116 longitudinal axis (of stylet 108)
118 notched section (of stylet 108)
120 sealing member
122 body (of sealing member 120)
124 extension(s) (of body 122 of sealing member 120)
130 first portion (of sealing member 120 at FIG. 9A)
131 opening (between first portion and second portion 140)
132 interior (of needle 100)
134 first direction
136 second direction
138 distal surface (of sealing member 120)
140 second portion (of sealing member 120 at FIG. 9A)
142 control mechanism
144 first Port (on Y-connector 142)
146 second Port (on Y-connector 142)
148 suction device
150 sealing component
152 larger, outer coiled region (of sealing member 120)
154 smaller, inner coiled region (of sealing member 120)
156 duck bill

The invention claimed is:

1. A device for tissue sampling, comprising:
   a needle including:
      i. a distal tip;
      ii. a proximal end; and
      iii. one or more interior portions,
   a stylet moveably supported within the one or more interior portions of the needle; and
   a sealing member moveably supported within the one or more interior portions of the needle, the sealing member substantially conforming to the one or more interior portions,
   wherein the needle extends along a longitudinal axis that extends between the distal tip and the proximal end,
   wherein the distal tip of the needle is configured to obtain a tissue sample,
   wherein the stylet and the sealing member are movable along the longitudinal axis, and movement of the stylet in a direction away from the distal tip creates a local vacuum at the distal tip so that the obtained tissue sample is aspirated into the one or more interior portions,
   wherein the sealing member comprises an outer coiled region and an inner coiled region, the outer coiled region substantially conforms to at least one of the or more interior portions, and
   wherein when the stylet is proximally moved, the inner coiled region collapses into the outer coiled region so that the local vacuum is created and the obtained tissue sample is aspirated into the one or more interior portions.

2. The device of claim 1, wherein the needle is a transbronchial needle.

3. The device of claim 1, wherein the device is free of an ancillary vacuum or suction source for creating the local vacuum.

4. The device of claim 1, wherein the proximal end of the needle is configured to connect to a vacuum source; and
   wherein the obtained tissue sample is aspirated into the one or more interior portions with the vacuum source, the local vacuum, or both.

5. A method comprising:
   orienting the distal tip of the needle of the device of claim 1 near a feature of interest;
   obtaining the tissue sample from the feature of interest;
   moving the stylet and the sealing member along the longitudinal axis away from the distal tip of the needle to create the local vacuum at the distal tip; and
   aspirating the sample into the one or more interior portions with the local vacuum.

6. The method of claim 5, wherein the moving step occurs before or after the obtaining step.

7. The method of claim 5, wherein the method includes a step of:
   providing a vacuum source at the proximal end of the needle; and
   wherein the aspirating step includes:
   aspirating the tissue sample into the one or more interior portions with the vacuum source, the local vacuum, or both.

8. The method of claim 5, wherein the method includes a step of:
   moving the stylet and the sealing member along the longitudinal axis towards the distal tip to expel the obtained tissue sample from the one or more interior portions.

9. A device for tissue sampling, comprising:
   a needle including:
      i. a distal tip;
      ii. a proximal end; and
      iii. one or more interior portions,
   a stylet moveably supported within the one or more interior portions of the needle; and
   a sealing member moveably supported within the one or more interior portions of the needle and substantially conforming to the one or more interior portions,
   wherein the needle extends along a longitudinal axis that extends between the distal tip and the proximal end,
   wherein the distal tip of the needle is configured to obtain a tissue sample,
   wherein the stylet and the sealing member are movable along the longitudinal axis, and movement of the stylet away from the distal tip creates a local vacuum at the distal tip so that the obtained tissue sample is aspirated into the one or more interior portions, wherein the sealing member is connected to at least one of the one or more interior portions of the needle, wherein the sealing member is adapted to stretch when the stylet is moved along the longitudinal axis away from the distal tip to create the local vacuum and aspirate the obtained tissue sample into the one or more interior portions, and wherein the sealing member stretches when the stylet is moved along the longitudinal axis towards the distal tip to expel the obtained tissue sample from the one or more interior portions.

10. The device of claim 9, wherein the needle is a transbronchial needle.

11. The device of claim 9, wherein the device is free of an ancillary vacuum or suction source for creating the local vacuum in the needle.

12. The device of claim 9, wherein the proximal end of the needle is configured to connect to a vacuum source; and wherein the obtained tissue samples are aspirated into the needle with the vacuum source, the local vacuum, or both.

13. A method comprising:

orienting the distal tip of the needle of the device of claim 9 near a feature of interest;

obtaining the tissue sample from the feature of interest;

moving the stylet and the sealing member along the longitudinal axis away from the distal tip of the needle to create the local vacuum at the distal tip; and aspirating the sample into the one or more interior portions with the local vacuum.

14. The method of claim 13, wherein the method includes a step of:

moving the stylet and the sealing member along the longitudinal axis towards the distal tip to expel the obtained tissue sample from the one or more interior portions.

15. A device for tissue sampling, comprising:

a needle including:
  i. a distal tip;
  ii. a proximal end; and
  iii. one or more interior portions, a stylet moveably supported within the one or more interior portions of the needle; and a sealing member moveably supported within the one or more interior portions of the needle, the sealing member substantially conforming to the one or more interior portions, wherein the needle extends along a longitudinal axis that extends between the distal tip and the proximal end, wherein the distal tip of the needle is configured to obtain a tissue sample, wherein the stylet and the sealing member are movable along the longitudinal axis, and movement of the stylet in a direction away from the distal tip creates a local vacuum at the distal tip so that the obtained tissue sample is aspirated into the one or more interior portions, wherein the sealing member comprises an outer coiled region, an inner coiled region, and a duck bill, the outer coiled region is configured to substantially conform to at least one of the one or more interior portions of the needle, wherein when the stylet is proximally moved, the inner coiled region is configured to collapse into the outer coiled region so that the local vacuum is created and the obtained tissue sample is aspirated into the one or more interior portions, and wherein the duck bill is configured to create an obstruction so that the obtained tissue sample is restricted from aspirating beyond the sealing member.

16. The device of claim 15, wherein the needle is a transbronchial needle.

17. The device of claim 15, wherein the device is free of an ancillary vacuum or suction source for creating the local vacuum.

18. The device of claim 15, wherein the proximal end of the needle is configured to connect to a vacuum source; and wherein the obtained tissue sample is aspirated into the one or more interior portions with the vacuum source, the local vacuum, or both.

19. A method comprising:

orienting the distal tip of the needle of the device of claim 15 near a feature of interest;

obtaining the tissue sample from the feature of interest;

moving the stylet and the sealing member along the longitudinal axis away from the distal tip of the needle to create the local vacuum at the distal tip; and aspirating the sample into the one or more interior portions with the local vacuum.

20. The method of claim 19, wherein the method includes a step of:

moving the stylet and the sealing member along the longitudinal axis towards the distal tip to expel the obtained tissue sample from the one or more interior portions.

* * * * *